United States Patent

Besselink et al.

[11] Patent Number: 5,551,871
[45] Date of Patent: Sep. 3, 1996

[54] TEMPERATURE-SENSITIVE MEDICAL/DENTAL APPARATUS

[76] Inventors: Petrus A. Besselink, Gronausestraat 1220, 7534 AT Enschede, Netherlands; Rohit C. L. Sachdeva, 2605 Courtside La., Plano, Tex. 75093

[21] Appl. No.: 64,953

[22] Filed: May 20, 1993

Related U.S. Application Data

[63] Continuation-in-part of Ser. No. 26,980, Mar. 5, 1993, abandoned.

[51] Int. Cl.$^6$ .................................................. A61C 5/00
[52] U.S. Cl. .................................................. 433/5; 606/78
[58] Field of Search ........................... 433/5, 17; 604/240, 604/281; 606/59, 78; 29/447, 381

[56] References Cited

U.S. PATENT DOCUMENTS

| | | | |
|---|---|---|---|
| 3,340,613 | 9/1967 | De Waskin | 433/5 |
| 3,740,839 | 6/1973 | Otte et al. | 29/628 |
| 3,759,552 | 9/1973 | Levinsohn et al. | 285/175 |
| 3,783,429 | 1/1974 | Otte | 337/393 |
| 3,786,806 | 1/1974 | Johnson. | |
| 3,861,030 | 1/1975 | Otte et al. | 29/626 |
| 3,872,573 | 3/1975 | Nichols et al. | 29/447 |
| 3,913,444 | 10/1975 | Otte | 85/8.3 |
| 4,001,928 | 1/1977 | Schweiso | 20/447 |
| 4,022,519 | 5/1977 | Hill | 339/30 |
| 4,035,007 | 7/1977 | Harrison et al. | 285/381 |
| 4,049,151 | 9/1977 | Schweiso | 220/201 |
| 4,149,911 | 4/1979 | Clabburn. | |
| 4,170,990 | 10/1979 | Baumgart. | |
| 4,198,081 | 4/1980 | Harrison et al. | 285/381 |
| 4,233,690 | 11/1980 | Akins. | |
| 5,044,947 | 9/1991 | Sachdeva et al.. | |

FOREIGN PATENT DOCUMENTS

| | | |
|---|---|---|
| 0145166 | 6/1985 | European Pat. Off.. |
| 0470660 | 2/1992 | European Pat. Off.. |
| 2648990 | 5/1978 | Germany. |
| 9200427 | 10/1993 | Netherlands. |

OTHER PUBLICATIONS

Articles entitled: "An Introduction to Martensite and Shape Memory", by C. M. Wayman and T. W. Duerig, pp. 3–20; "The Mechanical Aspects of Constrained Recovery", by J. L. Proft and T. W. Duerig, pp. 115–129.
"The Two–Way Shape Memory Effect", by Jeff Perkins and Darel Hodgson, pp. 195–206.
"The Use of Ni–Ti as an Implant Material in Orthopedics", by Dr. J. Haasters, Prof. G. v.Salis–Solio, and Dr. G. Bensmann, pp. 426–444.
"An Engineer's Perspective of Pseudoelasticity" by T. W. Duerig and R. Zadno, pp. 369–393.
"Wide Hysteresis Shape Memory Alloys", by T. W. Duerig, K. N. Melton and J. L. Proft, pp. 130–136.
"Shape Memory Alloy Tube and Pie Couplings", by Michael Kapgan and Keith N. Melton, pp. 137–148.
"The Design of Electrical Interconnection Systems with Shape Memory Alloys", by Ed Cydzik, pp. 149–157.
"Shape Memory Alloy Fastener Rings", by Tom Borden, pp. 158–169.
"Rotation Vector, A New Method for Representation of Three–Dimensional Deformity in Scoliosis", by Tatsuya Kojima, M.D., and Takahide Kurokawa, M.D., Ph.D., pp. 1296–1303.
"Luque–Galveston Procedure for Correction and Stabilization of Neuromuscular Scoliosis and Pelvic Obliquity: A Review of 68 Patients", by Yih–Lan Gau, John E. Lonstein, Robert B. Winter, Steven Koop, and Francis Denis, pp. 399–410.

(List continued on next page.)

Primary Examiner—Cary E. O'Connor
Attorney, Agent, or Firm—Wood, Herron & Evans P.L.L.

[57] ABSTRACT

A medical/dental apparatus utilizing the properties of shape memory materials to variably control the spatial relationship between two or more elements having portions which are proximately disposed and overlapping relative to one another. Another portion of each element is connectable to part of a patient's body.

64 Claims, 6 Drawing Sheets

OTHER PUBLICATIONS

"Das mechanische Prinzip des Fixateur externe zur dorsalen Stabilisierung der Brust–und Lendenwirbelsäule", by P. Kluger and H. J. Gerner, *Unfallchirurgie,* pp. 68–79, 1986.

"Posterior Stabilization with an Interlaminar Clamp in Cervical Injuries: Technical Note and Review of the Long Term Experience with the Method", in vol. 14, No. 3 of Neurosurgery, 1984, by Renn O. Holness, William S. Huestis, William J. Howes, and Roland A. Langille, pp. 318–322.

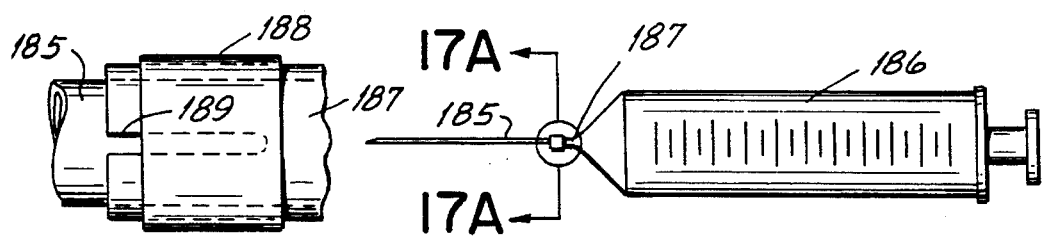
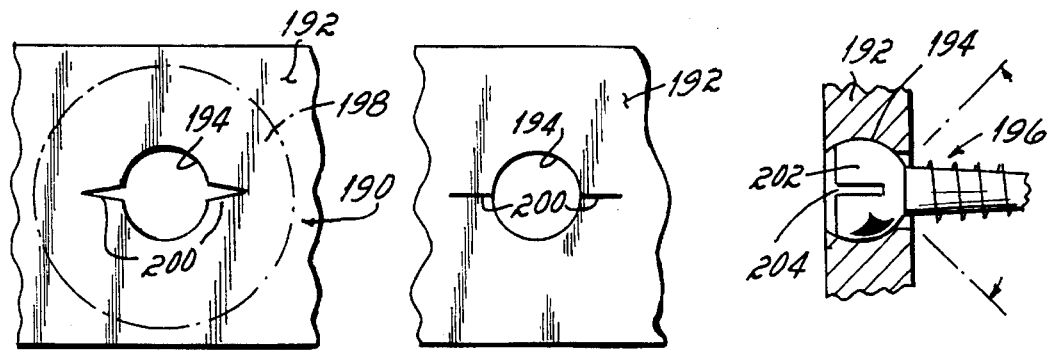
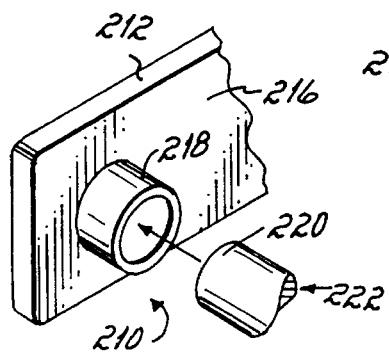
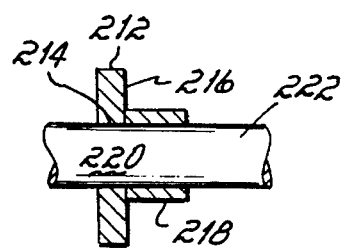
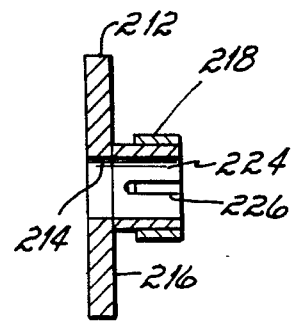
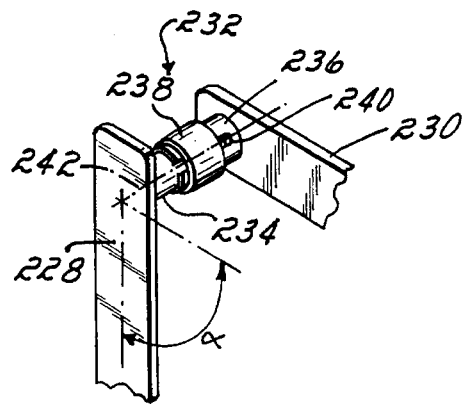
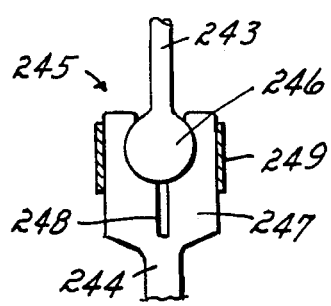

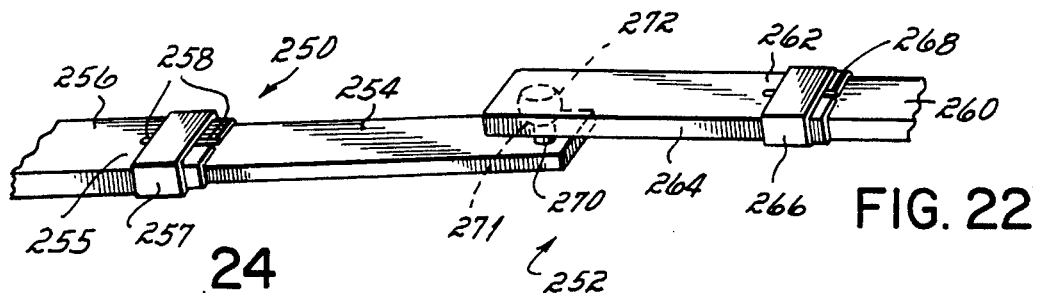
FIG. 22
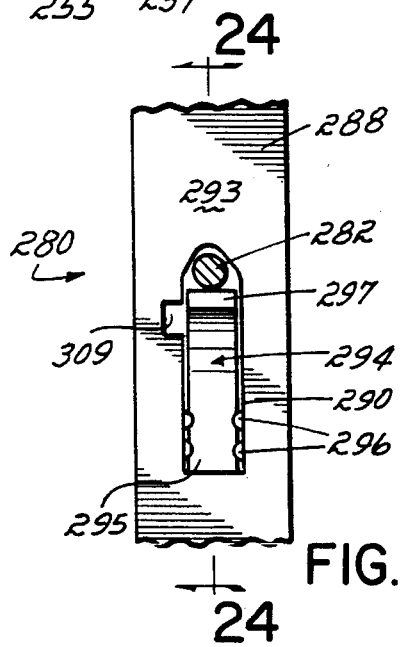
FIG. 23
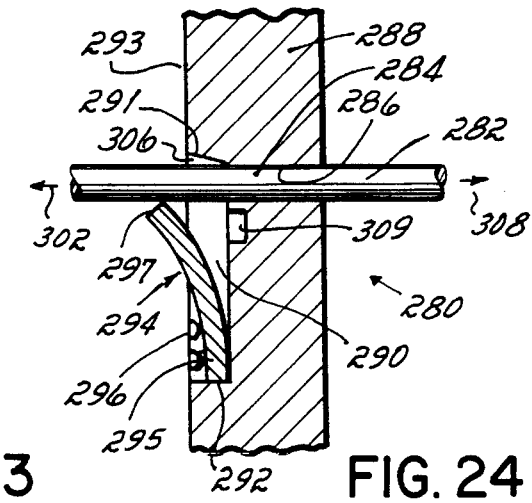
FIG. 24
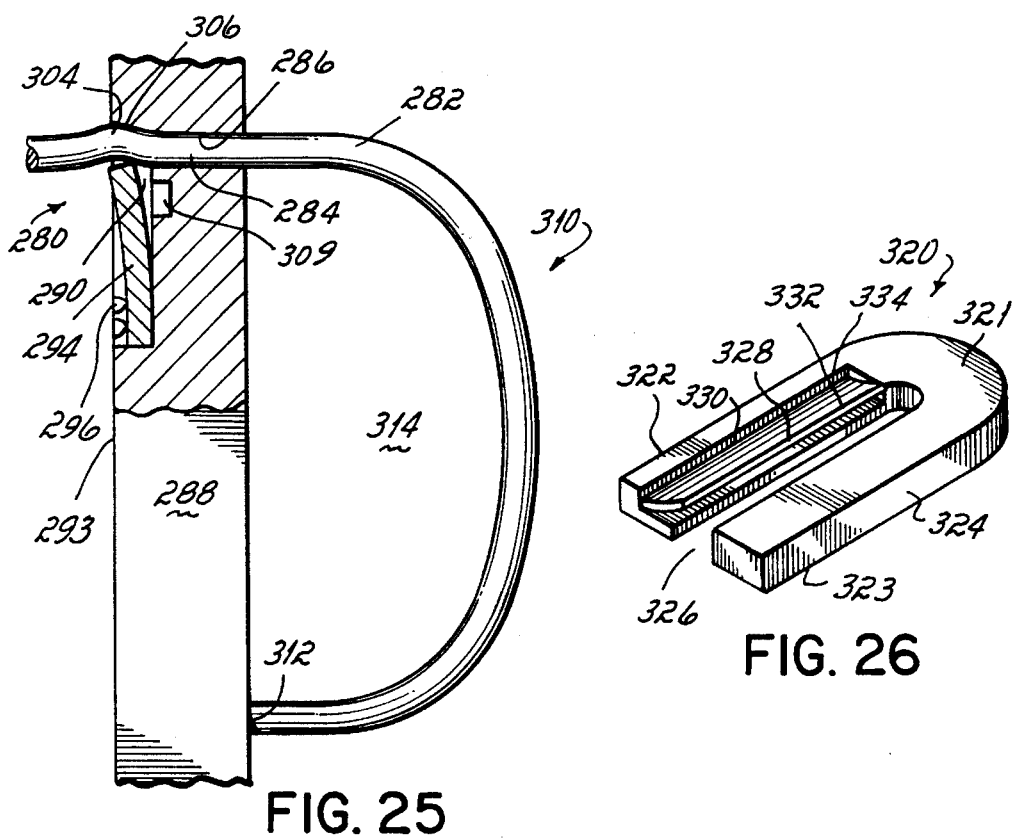
FIG. 25
FIG. 26

TEMPERATURE-SENSITIVE MEDICAL/DENTAL APPARATUS

RELATED APPLICATION

This application is a continuation-in-part application of United States patent application Ser. No. 08/026,980, filed Mar. 5, 1993.

FIELD OF THE INVENTION

The present invention relates to medical/dental apparatus with a temperature-sensitive adjustment system and, more particularly, to such an apparatus that is connectable to different parts of a patient's body.

BACKGROUND OF THE INVENTION

A variety of devices are used in the medical/dental field having multiple elements which are spatially adjustable relative to one another. A number of techniques and mechanisms have been used to effect these adjustments. By way of example, orthodontic head gears or face bows utilize such a technique to apply a correcting force to a patient's teeth. A face bow typically includes an outer bow fixed to an inner bow. The outer bow has two ends and an elastic element is looped around the back of the patient's neck and hooked onto the ends of the outer bow in order to supply a hold-down force to particular teeth of the patient through the inner bow. The inner bow typically has tubular ends, each of which telescopically receive a face bow wire, with the wire fixed thereto. The inner bow is usually placed in the patient's mouth at about the level of the canine teeth. The protruding end of each face bow wire is attached, at the rear of the mouth, to whichever molar is to be moved by inserting the wire end into a small buccal tube which has been attached to the molar by means of a band. In this manner, the wire can apply a rearward corrective force to the molar by limiting relative movement between each of the wires and the inner face bow. The end of the wire is free to slide axially inside the tube. Therefore, limitation of this relative movement is achieved by making a loop in each of the face bow wires which cannot slip through the respective buccal tubes. Each loop thus serves as a stop enabling the corrective force to be applied. The wire can also be bent to place the free end of the loop at a desired angle to the fixed end of the wire in order to change how the corrective force is applied to the molar (i.e., to achieve the desired movement of the tooth).

At intermediate visits, the orthodontist previously had to regularly bend the loop in order to make corrections to the force being applied. In particular, the bow length is increased or decreased by curving the loop more or less. A number of such bending procedures, in many cases, results in breakage of the wire near the loop due to fatigue of the wire material. While such failures result in additional work and costs, it also is dangerous and potentially detrimental to the patient's health, for example, a piece of wire may break off and end up in the patient's throat. The presence of the loops inside of the patient's mouth has also been found to be unpleasant for some patients. Thus, there is a need for a different technique or mechanism for adjusting each of the face bow wires relative to the inner face bow that avoids having to repeatedly deform the wires and eliminate the need for the loops.

With many of these devices, the first and second elements are telescopically engaged with each other. With one such device, a Herbst appliance, one element includes a pin and the other element includes a tube. One end of the pin is slidably received by one end of the tube. Two pin/tube combinations are used, one on either side of the patient's mouth to make corrections in the relative position of the patient's upper and lower mandible. On each side of the patient's mouth, the other end of the pin is mounted to a patient's tooth on the lower mandible and the other end of the tube is mounted to a tooth on the upper mandible. Relative telescopic movement between each pin and tube is limited by inserting a stop, such as a shorter length of smaller diameter tube, into the tubular element. It is often desirable to adjust how deep one or both of the pins can slide into their respective tubes. To accomplish this adjustment, it is often necessary to remove one or both of the Herbst elements from the patient's mouth before the changes can be made. Having to remove one or both of the Herbst elements from the patient's mouth tends to prolong the treatment period. In addition, even once removed, the prior Herbst elements are not readily adjustable. Other adjustable telescoping devices in the medical/dental field suffer from similar problems. Therefore, there is a need for a device or system which can avoid these problems.

Another example of such devices includes scoliosis correction systems for stabilizing the patient's spine. Such systems often include sets of dual spinal hooks for attachment to the patient's vertebra. Each set of hooks is mounted to a stabilization or correction bar positioned along the patient's spine. Threaded bolts or screws have been used to adjust the hooks relative to one another in each set. In addition, set screws have been used to fix the location of each set of hooks along the stabilization bar. However, the threads of these bolts and screws have a tendency to strip or gall and their installation can be cumbersome because there is not much room to use the tools necessary to adjust these screws and bolts. In addition, the screws have been known to have a tendency to back-out in in-vivo situations. This could cause the device to loosen, requiring additional surgery.

A number of medical/dental devices are fastened directly into a patient's bone structure. For example, Osteogenesis distraction devices typically include at least one mounting plate with one or more holes formed therethrough for receiving a fastener, like a screw, which is anchored into the patient's bone. It has been found that with time the screw has a tendency to back out of the plate hole. Therefore, there is also a need to limit movement of the screw, once inserted into the patient's bone, relative to the mounting plate.

SUMMARY OF THE INVENTION

An objective of the present invention is to provide a medical/dental apparatus for more easily adjusting the spatial relationship between at least two parts of a body.

An additional objective related to the preceding objective is to provide such a medical/dental apparatus which is able to more reliably maintain the spatial relationship between the body parts.

Another related objective is to provide such a medical/dental apparatus which allows the spatial relationship between the body parts to be repeatedly varied with the apparatus being less likely to fail.

A further objective of the present invention is to provide a medical/dental apparatus for transmitting a wider range and variety of forces between at least two body parts.

An additional objective related to the directly preceding objective is to provide such a medical/dental apparatus which can more reliably maintain the applied force.

Another related objective is to provide such a medical/dental apparatus which allows the applied force to be repeatedly varied with the apparatus being less likely to fail.

An additional related objective is to provide such a medical/dental apparatus which can more easily vary the force being applied between the body parts.

A further objective of the present invention is to provide a medical/dental apparatus which can be more reliably secured to at least two parts of a patient's body, and more particularly, two parts of the same bone or different bones.

The above objectives of the present invention are attained by providing a medical/dental apparatus which includes a first element and a second element, each having a portion connectable to part of a patient's body. Other portions of these elements are proximately disposed and overlapping relative to one another in a variable spatial relationship. A third or shape memory element, made of a shape memory material having a transformation temperature range, is used to allow or limit adjustment of the spatial relationship between the first and second elements. The shape memory element limits adjustment of the spatial relationship when the temperature of the shape memory material is at a working or ambient temperature. The shape memory element allows adjustment of the spatial relationship by either increasing or decreasing the temperature of the shape memory material relative to the working temperature.

Shape memory materials are generally relatively weak and pliable at least when the material is at a temperature below the transformation temperature range and relatively strong with superelastic properties at least when the material is at a temperature above the transformation temperature range. The properties of a given shape memory material typically vary within the transformation temperature range. Generally, the strength and superelastic characteristics tend to increase toward the high temperature end of the transformation temperature range and decrease toward the low temperature end. Characteristics of such shape memory materials are well documented. For example, see the following published works: a book entitled *Engineering Aspects of Shape Memory Alloys*, 1990, published by Butterworth and Heinemann and edited by T. W. Duerig, K. N. Melton, D. Stockel and C. M. Wayman (ISBM No. 0-750-61009-3), including articles therein entitled "An Introduction to Martensite and Shape Memory", by C. M. Wayman and T. W. Duerig, pages 3–20; and "The Mechanical Aspects of Constrained Recovery", by J. L. Proft and T. W. Duerig, pages 115–129, each of which are incorporated by reference herein in their entirety.

Briefly, the working or ambient temperature (e.g. normal body temperature) of a device according to the principles of the present invention can be below, within or above the transformation temperature range (TTR) of the shape memory material(s) being used. The TTR for many shape memory materials, especially shape memory metal alloys, can often be adjusted to compensate for a particular ambient temperature.

With respect to most shape memory metals, two basic crystal structures exist, martensite below the TTR and austenite above the TTR. A combination of both structures, to varying degrees, exist within the transformation temperature range. Generally, martensite is relatively weak and pliable, and austenite is relatively strong with superelastic properties. If the shape memory metal is in the martensitic stage, it will need to be heated to transform to austenite. If the shape memory metal is in the austenitic stage, it will need to be cooled to transform to martensite. When the ambient temperature is within the TTR, the actual structure of the shape memory metal is dependent on its temperature history. When the structure of the shape memory metal is not all but mostly austenite, it can still exhibit superelastic properties. When the structure of the shape memory metal is all or mostly martensite, it may be comparatively weaker and more pliable than the austenite structure, but it can still exhibit some elastic properties (i.e., strained to produce an applied force). Some shape memory metals, commonly known as wide hysteresis alloys (e.g., titanium-nickel-niobium) can have a wide TTR. With these materials, it is possible to use the martensitic structure during insertion at ambient temperature, thereby enabling adjustment without cooling. Once the adjustment is complete, the memory material is temperature cycled (typically by heating above the TTR) to drop the austenite-to-martensite transformation to a temperature well below ambient temperature. The locking affect would therefore be stable, even at a range of ambient temperatures. This type of shape memory material is particularly useful when the environment is inside a patient's body (e.g., a scoliosis correction system) where repeated adjustment is often not necessary or desirable but stability is.

According to the principals of the present invention, the first and second elements can have a variety of structures. The proximate portion of one element can be telescopically disposed inside of the proximate portion of the other element, such as in Herbst appliances. In addition, proximate portions of the first and second elements can be disposed alongside each other, such as the inner and outer bow of a face bow headgear. The structure of the shape memory element is, at least in part, dictated by the structure of the proximately disposed portions of the first and second elements. In one broad embodiment of the invention, the shape memory element is disposed around both proximately disposed portions of the first and second elements. In another broad embodiment, the shape memory element may be disposed around a portion of only one of the other elements. In still another embodiment, the shape memory element is disposed between the first and second elements. In addition, the shape memory element may even be part or all of the proximate portion of one or both of the first and second elements.

The shape of the shape memory element may be pre-programmed or trained such that the shape memory element will forcefully return to its pre-programmed shape when heated from below to above the transformation temperature range. Many, if not all, shape memory materials may also be trainable so that the shape of the shape memory element returns to a pre-programmed shape when cooled from above to below the transformation temperature range. Because shape memory materials are relatively more deformable at temperatures below their transformation temperature range, the later shape memory element will likely not return to its pre-programmed shape nearly as forcefully as the former shape memory element. For the many possible device embodiments incorporating principles of the present invention, the temperature sensitive characteristics of the shape memory material are used to help maintain the spatial relationship between the proximately disposed portions of the first and second elements while still enabling the spatial relationship between these elements to be repeatedly adjusted. Depending on the application, it may be preferable to train the shape memory element to allow adjustment of the spatial relationship when heated in order for the shape memory element to have superelastic properties at ambient temperature. However, there may also be applications where adjustability below ambient temperature is desirable and superelastic properties not necessary.

One feature of the present invention is to position a biasing sleeve between the shape memory element and, depending upon the device embodiment, one or both of the proximately disposed portions of the first and second elements. This intermediate sleeve helps to insure that the spatial relationship of the proximate element portions will be easily adjustable at least when the shape memory material is cooled below its TTR. The sleeve accomplishes this by stretching the shape memory element when the shape memory material is in its pliable state.

A related feature to the previous feature is to position a biasing sleeve around the outside of the shape memory element, with the shape memory element being disposed around one or both of the proximately disposed portions of the first and second elements, depending upon the device embodiment. This outer biasing sleeve is used when the shape memory element is trained to have a shape which limits adjustment of the spatial relationship of the proximate element portions when the shape memory material is cooled, at least to below its TTR. The outer sleeve accomplishes this by compressing the shape memory element when the shape memory material is in its pliable state.

Another feature of the present invention, is the use of a biasing spring for moving the first and second element relative to one another at least when the temperature of the shape memory element drops below its transformation temperature range. For some device embodiments, it may be desirable to make the biasing spring out of a shape memory material to take advantage of either or both of the materials superelastic or shape memory properties.

A further feature of the invention is the use of a mechanical aide to the shape memory element in limiting the rotation of the proximately disposed portions of the first and second elements relative to one another about a common axis.

Another feature of the invention is to structurally weaken one or the other of the proximately disposed portions of the first and second elements, such as with an aperture or slot. This is done in order to make it easier for the shape memory element to prevent, or at least limit, adjustment of the first and second element portions at least when the temperature of the shape memory element is above its transformation temperature range.

The above and other aspects of the present invention will become apparent upon consideration of the following descriptions taken in conjunction with the accompanying drawings.

BRIEF DESCRIPTION OF THE DRAWINGS

FIG. 17 is an elevational view of a syringe and a hypodermic needle according to the present invention;

FIG. 17A is the encircled area 17A of FIG. 17 showing a needle connector according to the present invention;

FIGS. 18A and 18B are elevational views of a connecting system according to the present invention in an open and locked condition, respectively;

FIG. 18C is a partially sectioned side view of an alternative embodiment of the connecting system of FIGS. 18A and 18B with a ball-headed screw fitted therein;

FIG. 19 is a perspective view of an alternative connecting system according to the present invention;

FIG. 19A is a partially sectioned side view of one embodiment of the connecting system of FIG. 19;

FIG. 19B is a sectional side view of an alternative embodiment of the connecting system of FIG. 19;

FIG. 20 is a diagrammatic perspective view of a lockable joint according to the present invention;

FIG. 21 is a partially sectioned side view of a lockable ball joint according to the present invention;

FIG. 22 is a diagrammatic perspective view of an adjustable and lockable articulating members according to the present invention;

FIG. 23 is a partially sectioned front view of a connecting system incorporating the principles of the present invention;

FIG. 24 is a partially sectioned side view taken along lines 24—24 of FIG. 23;

FIG. 25 is a partially sectioned side view of a particular application of the connecting system of FIG. 23; and FIG. 26 is a perspective view of a modification of the connecting system of FIG. 23.

DETAILED DESCRIPTION OF THE INVENTION

Figure 1:
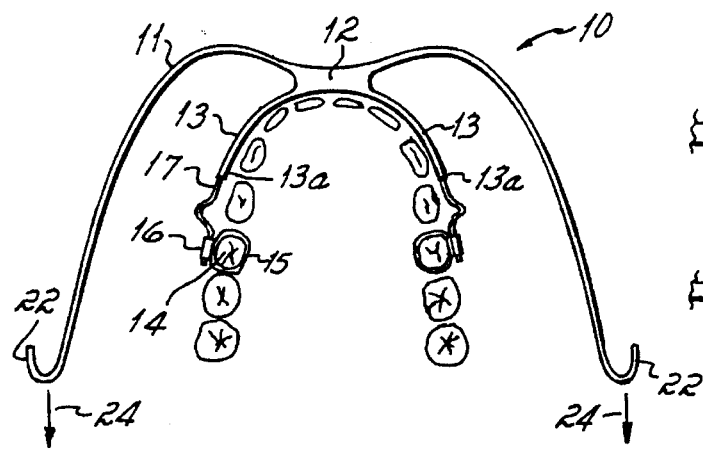
FIG. 1 is an elevational view of an orthodontic face bow attached to upper molars in a patient's mouth.

The following is a detailed description of a variety of medical/dental devices incorporating principals of the present invention. Referring to FIG. 1, a face bow headgear 10 is shown having an outer bow 11 connected to an inner bow 13 such as by a weld or solder joint 12. The inner bow 13 can be made solid with an axially bore in either end 13a or made tube-shaped over its entire length. A face bow wire 17 is fitted into either end of the inner bow 13 and immovably connected thereto. Each face bow wire 17 is connected to a molar 14 for having a correction force transmitted thereto. A band 15 is mounted around each molar 14 and each wire 17 is connected to its respective molar 14 through a buccal tube 16 attached to the band 15. The ends 22 of the outer bow 11 are hooked for receiving an elastic band (not shown) which extends around the back of a patient's neck. The elastic band applies a force in the direction indicated by arrows 24 in order to provide the correction force transmitted through face bow wires 17 to the molars 14.

Figure 2:
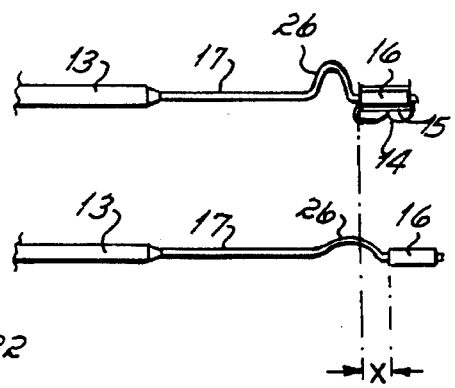
FIG. 2 is a side view of an inner bow and face bow wire showing a prior technique for adjusting the length of the wire.

Referring to FIG. 2, the face bow wire 17 is supported axially against tube 16 by a curve 26 in the wire 17. The curve 26 acts as a stop in preventing the wire 17 from extending completely through the tube 16. By changing the shape of the curve 26 in wire 17, the effective length of the wire 17 can be adjusted by a length X. When bent repeatedly, this results in the above-mentioned fatigue problems which lead to breakage of wire 17. It is often desirable to have a different correction force applied to each molar 14, such as by making the effective length of one wire 17 different from the other wire 17. This can be accomplished by shaping each curve 26 differently, but the potential fatigue problem would still exist.

Figure 3:
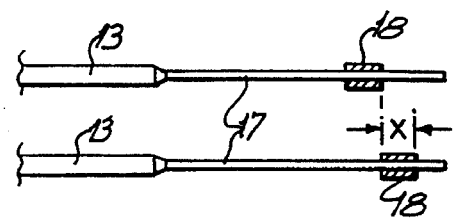
FIG. 3 is a side view of an inner bow and face bow wire showing a shape memory element according to the present invention for adjusting the length of the wire.

Referring to FIG. 3 according to the principles of the present invention, the curve 26 can be replaced by a clamping ring or sleeve 18 made of a shape memory material having a transformation temperature range. Being made out of such a shape memory material, the clamping sleeve 18 can be moved axially along the wire 17 a desired correction length X without deforming the wire 17 as in the previous practice. As is well-known in the art and therefore will not be discussed in detail herein, articles made of such shape memory materials are pliable and can typically be readily reshaped at temperatures below the transformation temperature range. Such articles can also be trained to have a pre-programmed shape which the article will change into at least when the material reaches a temperature above its transformation temperature range. Thus, after being reshaped, the article can be made to forcely return to its pre-programmed shape when heated up to above its transformation temperature range. As is well-known, bringing the temperature of the shape memory material to within its transformation temperature range will result in varying degrees of the aforementioned pliability and pre-programmed shape obtained, depending upon the temperature reached.

Therefore, by pre-programming the sleeve 18 with an inside diameter smaller than the outside diameter of the wire 17, the sleeve 18 can be cooled until the shape memory material becomes readily pliable and the axial position of the sleeve 18 easily adjusted. Once at a desired axial position, the sleeve 18 can then be heated up until at least a sufficient degree of its pre-programmed shape and superelastic properties are attained that the sleeve 18 grips the wire 17 with sufficient force to act as a satisfactory stop. The superelastic properties of the shape memory material enables significant recoverable strains, and therefore gripping forces, to be developed by the sleeve 18. The axial position of the sleeve 18 can be repeatedly adjusted by simply cooling and then heating the sleeve 18 to the appropriate temperatures. There are a wide variety of shape memory materials, including shape memory metal alloys (e.g. titanium based alloys and iron based alloys) and shape memory polymers, which have a wide range of possible transformation temperature ranges. Selection of an appropriate shape memory material will depend, in large part, on the necessary material properties for the particular application and the working environment of the device.

Figure 4:
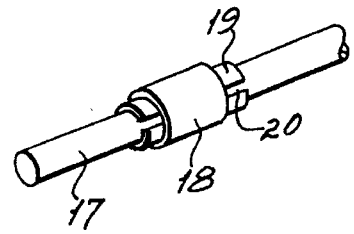
FIG. 4 is a perspective view of the shape memory element of FIG. 3 including a biasing sleeve.

Referring to FIG. 4, if desired, the memory ring 18 can be integrated with an intermediate spring or biasing sleeve 19 positioned between the wire 17 and the spring 19. The biasing sleeve 19 preferably includes a longitudinal slot 20 to provide additional spring-like characteristics and can be made of standard spring material or even a shaped memory material exhibiting superelastic characteristics. A spring having superelastic properties exhibits very flat mechanical characteristics. With the biasing sleeve 19 inside of the memory ring 18, when the shape memory material is cooled down the memory ring 18 is stretched by the spring 19 making axial movement of the memory ring 18 along the wire 17 easier.

Figure 4A:
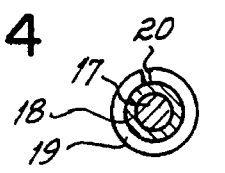
FIG. 4A is a perspective view of an alternative use of a biasing sleeve like that shown in FIG. 4.

Referring to FIG. 4A, the memory ring 18 can be mounted directly onto wire 17 and the biasing sleeve 19 disposed around the outside of ring 18. With this construction, shape memory ring 18 is trained to have a smaller inside diameter than the diameter of wire 17 when cooled and to have a larger inside diameter than the diameter of wire 17 when heated, to at least temperature below and above the TTR, respectively Thus, when the ring 18 is cooled it grips wire 17 Because most if not all shape memory materials are weaker and more pliable at temperatures below the TTR, the gripping strength of ring 18 may not be sufficient for the particular application. Biasing sleeve 19 would then be used to provide whatever additional crimping force was necessary for ring 18 to function as an adequate stop. To adjust its position, ring 18 is heated until it transforms sufficiently to overcome biasing sleeve 19 and expands to the point of being slidable along wire 17. Thus, the embodiment in FIG. 4 can be used when it is desirable to cool the ring 18 below the ambient temperature in order to make adjustments, and the embodiment in FIG. 4A can be used when it is desirable to heat the ring 18 above the ambient temperature in order to make adjustments.

Figure 5:
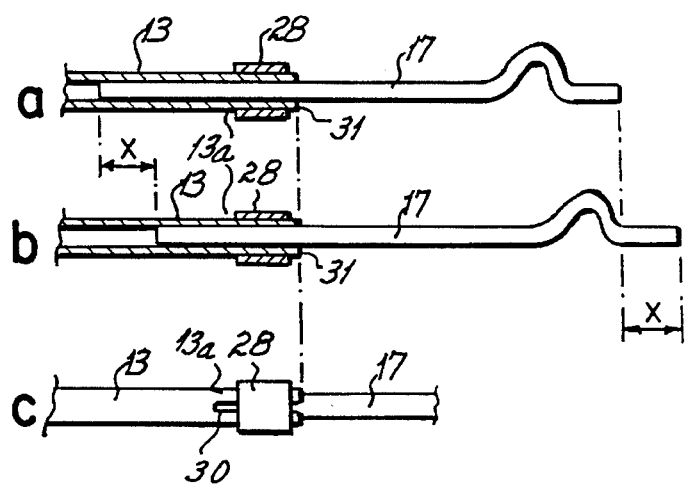
FIGS. 5a, 5b; and 5c are side views of an inner bow and a face bow wire showing another shape memory element according to the present invention for adjusting the length of the face bow wire relative to the inner bow.

Referring to FIGS. 5a, 5b and 5c, the face bow 10 can be modified to allow the length of each wire 17 to be adjusted by varying the depth of the wire 17 inside of the respective ends 13a of the inner bow 13. In this way, each tubular end section 13a of the inner bow 13 can serve as a biasing sleeve like sleeve 19 by placing another shape memory clamping ring or sleeve 28 around the outside of each tubular end 13a with the wire 17 inserted therein. It is desirable for at least one and preferably two longitudinal slots or apertures 30 to be formed through the wall 31 of each tubular end 13a so that the wall 31 is more resilient and behaves more like the spring sleeve 19.

Like sleeve 18, sleeve 28 can be cooled down a sufficient amount to allow the wire 17 to be moved an axial distance X. Heating up the sleeve 28 to an appropriate temperature will likewise cause it to shrink, pressing the springy ends 13a of the inner bow 13 down tightly onto the wire 17 fixing the axial position of the wire 17 relative to the inner bow 13. Thus, the wire 17 can be given the appropriate curve 26 and length without having to be bent again. While it may cause a patient some discomfort, using a curve 26 enables the wire 17 to retain some axial elasticity. The curve 26 can also be eliminated and a more permanent axial stop used, like, for instance, a small soldered ring (not shown).

This freedom to move the wire 17 axially within the tubular end 13a of the inner bow 13 also has other advantages. Standard face bow wire 17 are typically made of stainless steel. With the wires 17 permanently fixed to the inner bow 13, any change in the material for wire 17 would necessitate the replacement of the entire face bow headgear 10. Now, the wires 17 can be readily replaced, for whatever reason, and the inner and outer bows 13, 11 recycled. As previously stated, it may be desirable to apply different forces to each of the molars 14. For the same wire structure, a wide range of mechanical properties for the wire 17 can be obtained by varying the wire material used. Rather than varying the length or shape of each wire 17 to obtain this difference in correction forces, different wire materials can be used.

Figure 7:
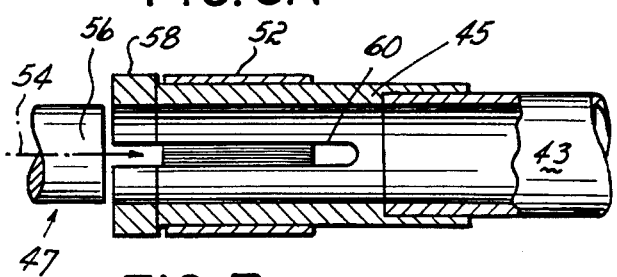
FIG. 7 is a side partially sectioned view of one end of the inner bow of FIG. 6 with a face bow wire about to be inserted.
Figure 7A:
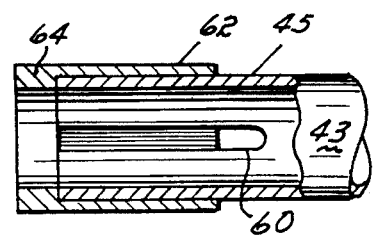
FIG. 7A is a partially sectioned side view of an alternative embodiment of one end of the inner bow of FIG. 6.
Figure 8:
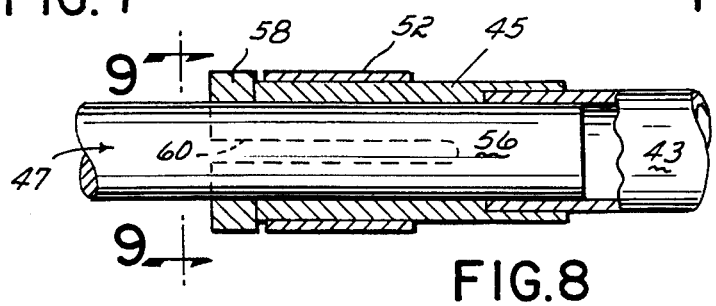
FIG. 8 is a view similar to FIG. 7 with the face bow wire inserted into the inner bow.

Referring to FIGS. 6–10, another face bow headgear 40 is shown incorporating principals of the present invention. The face bow 40 includes an outer bow 41 and an inner bow 43. Either end of the outer bow 41 is hooked for being connected with a conventional neck strap (not shown). The inner bow 43 has tubular sections 45 at its ends. These tubular sections 45 can be the actual ends of the inner bow 43, as in the previous face bow 10 (see also FIG. 7A) or separate pieces which are integrally joined to the ends of the inner bow 43, as shown in FIGS. 7 and 8. If separate pieces, each tubular section 45 can be made of any acceptable spring material, including a shape memory material exhibiting superelastic properties. Using such separate tubular sections 45 enables the balance of the inner bow 43 to be more generic, thereby reducing costs. Each tubular section 45 is adapted to telescopically receive one end of a face bow wire 47 therein. The other end of each wire 47 is inserted into a buccal tube 46 and is free to slide therethrough, in the same manner as previously described. The tube 46 is fixed to a band 48 mounted around a molar 50. Each wire 47 includes some form of stop 51, such as a curve in wire 47 or a shape memory ring, to limit axial sliding through tube 46. As in the embodiment of the present invention shown in FIGS. 5a, 5b and 5c, a shape memory ring or sleeve 52 is used to allow the length of the wire 47 to be axially adjusted by varying the depth of the wire 47 inside of the tubular section 45 of the inner bow 43.

Figure 6:
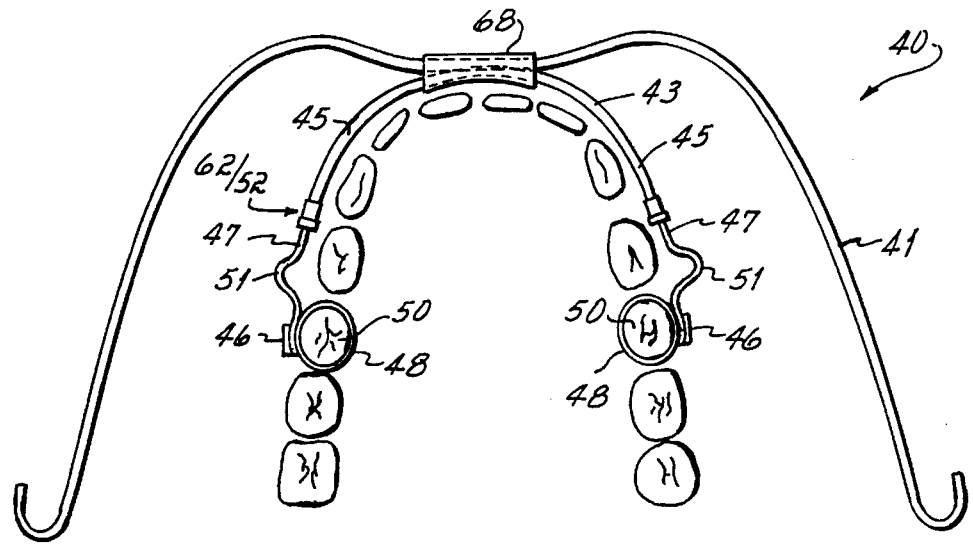
FIG. 6 is an elevational view of one embodiment of a face bow according to the present invention.
Figure 6A:
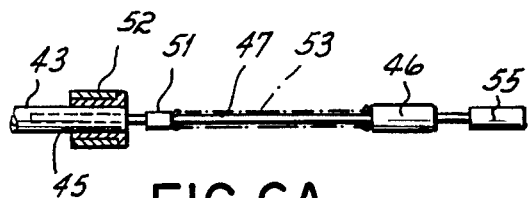
FIG. 6A is a side partially sectioned view of an inner bow and a preloaded face bow wire of the face bow embodiment of FIG. 6.

Referring to FIG. 6A, either or both wires 47 can be preloaded by positioning a compression coil spring 53 around wire 47 between the stop 51 and buccal tube 46. Stop 51 is made of shape memory material like stop 18 (see FIG. 3). To prevent wire 47 from being forced out of buccal tube 46, the other end of each wire 47 extends out of tube 46 and mounts another stop 55 which may or may not be shape memory. Thus, with the headgear 40 in place in a patient's mouth and secured around the patient's neck, each spring 53 can apply a corrective force to one of the molars 50. Whichever is desirable, spring 53 can be made of a super-elastic material or standard spring materials. In addition, if it is desirable for inner bow 43 to apply asymmetrical corrective forces, different strength springs 53 can be used or only one wire 47 fitted with the spring 53 in this manner. By using a shape memory stop 51, the force exerted by spring 53 can be adjusted by changing the position of stop 51 along wire 47.

Figure 9:
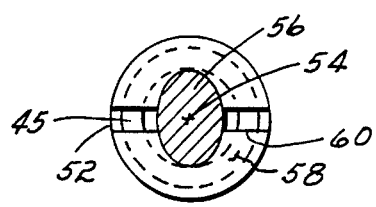
FIG. 9 is a sectional view taken along lines 9—9 of FIG. 8 showing one embodiment of the rotational limitation means of the present invention.
Figure 9A:
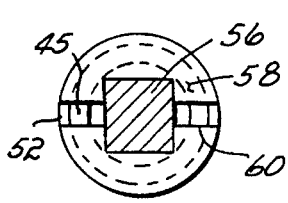
FIG. 9A is a view similar to FIG. 9 of another embodiment of the rotational limitation means of the present invention.

Unlike the previous facebow headgear embodiment of FIGS. 1–5, each wire 47 in the embodiments of FIGS. 7–9 is unable to rotate within its respective tubular section 45 about an axis 54 common to both the tubular section 45 and the one end of the wire 47 telescopically disposed inside the section 45. This rotational limitation is accomplished by making the cross-section of at least a part or length 56 at the one end of each wire 47 non-circular. In addition, at least a portion 58 of the tubular section 45 of the inner bow 43 likewise has an opening that is non-circular perpendicular to the common axis 54. The portion 58 can be a separate piece attached to the tubular section 45 or an actual portion or all of the tubular section 45. Preferably, the wire length 56 and tubular portion 58 have the same shape, for example, oval (as shown in FIG. 9) or rectangular (as shown in FIG. 9A). Because their cross sections are non-circular, the wire length 56 is not rotatable inside the tubular portion 58. Thus relative rotation of the wire 47 and bow 43 can thereby be prevented, or at least limited, regardless of the temperature of the ring 52

Preferably, each buccal tube 46 and the other end of each face bow wire 47 also have at least a portion 58 and at least a part or length 56, respectively, with such non-circular cross sections. By limiting rotation of each wire 47 within its respective tubular section 45 and buccal tube 46, a greater variety of correction forces, including torques, can be applied in more ways to either one or both molars 50. As in the previous embodiment, the wall of the tubular section 45 at the end of the inner bow 43 can have at least one and preferably two longitudinally slots or apertures 60 formed therethrough Preferably, the slot 60 is also formed through the tubular portion 58.

In an alternative embodiment (see FIG. 7A), a different shape memory ring or sleeve 62 can be used having its own tubular portion 64 which is similar to tubular portion 58. While a face bow headgear has been specifically described, the above disclosure relative to the inner bow 13 is also applicable to lip bumpers (not shown), which are very similar in structure.

Figure 6B:
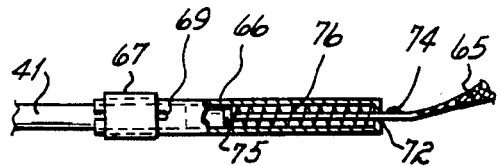
FIG. 6B is a side partially sectioned view of an outer bow and preloaded neck strap of the face bow embodiment of FIG. 6.

Referring to FIG. 6B, rather than using a conventional method to connect the ends of a neck strap 65 to the ends of the outer bow 41 of headgear 40, the principles of the present invention can be followed. First, outer bows 41 with straight rather than hook ends are used. Each straight end of the face bow 41 is telescopically disposed inside of one end of a tube 66 and adjustably fixed thereto with a shape memory ring 67 and, if desirable, a longitudinal slot 69, as previously described. The other end of the tube 66 is closed except for a concentric hole 72 formed therethrough. A pin 74 is fixed to each end of the strap 65 and disposed inside of tube 66 through hole 72. The free end of each pin 74 mounts a stop 75. A compression coil spring 76 is disposed around the portion of pin 74 inside of tube 66 and between stop 75 and the other end of tube 66. Depending upon the mechanical properties desired, spring 76 can be made of any suitable spring material including a superelastic shape memory material, like the other springs previously described. Thus, each spring 76 can be preloaded to apply a corrective force to each of the molars 50. Likewise, a previously discussed, asymmetrical corrective forces could also be applied to molars 50. To prevent injury or discomfort to the person wearing head gear 40, shape memory ring 67 may be designed to apply a minimal clamping force so that each tube 66 can be pulled off of outer bow 41 during overload conditions (e.g., strap 65 being pulled from behind) to avoid injury to the patient. If this is done, the force exerted by spring 76 would necessarily have to be less than the crimping force exerted by ring 67.

Figure 10:
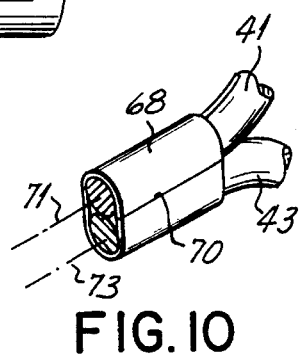
FIG. 10 is a partially sectioned perspective view of a shape memory element connecting the inner and outer bows of FIG. 6.

Referring to FIG. 10, rather than connecting the inner and outer bows 43, 41 with a weld or solder joint (like joint 12 in FIG. 1), a middle portion of outer bow 41 and inner bow 43 are proximately disposed alongside each other and encircled with a band or ring 68 made of a shape memory material according to the principals of the present invention. Preferably, the band 58 is split longitudinally along line 70, for ease of assembly. As with the previous shape memory sleeves, band 68 preferably has a pre-programmed shape such that when the shade memory material is heated to an appropriate temperature, the middle portions of the bows 41 and 43 are gripped tightly together by band 68 in their proximately disposed relationship. In this way relative axially movement of the bows 41, 43 along their respectively central axes 71, 73 can be allowed for adjustment purposes and then prevented, or at least limited, for use. In addition, rotation of each bow 41, 43 about its axes 71, 73 can also be allowed or prevented, or at least limited, by band 68. The use of band 68 increases the versatility of the head gear 40 by enabling either bow 41, 43 to be replaced independent of the other and their spatial relationship easily adjusted. In addition, this versatility enables two devices to be incorporated into one. Namely, the head gear 40 can be used as a complete face bow head gear or the inner bow 43 can be removed and used as a lip bumper (not shown). Standard bows 41, 43 are typically each made of stainless steel. Some patients have been known to feel some discomfort due to their sensitivity to nickel leaching from the stainless steel material. In addition, stainless steel may not have the mechanical properties felt necessary to apply the appropriate corrective forces to the patient's molars 50. The use of band 68 thus enables composite head gears 40 to be easily constructed which have bows 41, 43 made of different materials and oriented in different spatial relationships in order to provide greater versatility. A shape memory band like band 68 may have a number of other applications, including as a clamp in forming a cerclage wire (i.e., a loop of wire with the ends cramped together).

Figure 11:
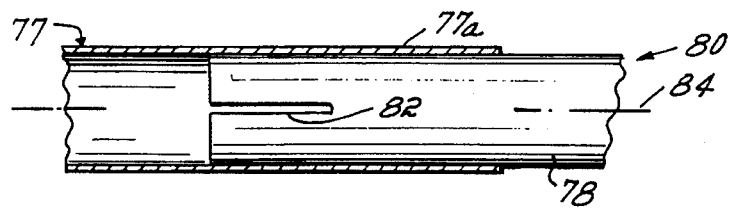
FIG. 11 is a partially sectioned side view of an alternative embodiment for variably locking two elements according to the present invention.

Referring to FIG. 11, rather than using a shape memory ring or sleeve to lock two telescoping elements of a device together, as in the previous embodiments, a tubular section 77a of a second element 77 or a telescopically received portion 78 of a first element 80 may be variably locked together by making one or the other or both portions 77a and 78 out of a shape memory material. If tubular section 77a is made of shape memory material which shrinks when heated to ambient temperature, it is preferable for portion 78 to be solid. If portion 78 is made of the shape memory material and tolerances are kept tight, it is also preferable for portion 78 to be solid. If, however, the tolerances between portion 77a and 78 are not tightly controlled, it may be preferable to form a longitudinal slot or aperture 82 in shape memory portion 78 and pre-program portion 78 so that the slot 82 becomes wider when heated to ambient temperature. Even greater locking forces can be attained by making both portions 77a and 78 out of shape memory material. Thus, relative axial movement along axis 84 or relative rotational movement about axis 84 can be allowed or limited. This basic combination of elements could thus be used to control rotation within a joint.

Figure 12:
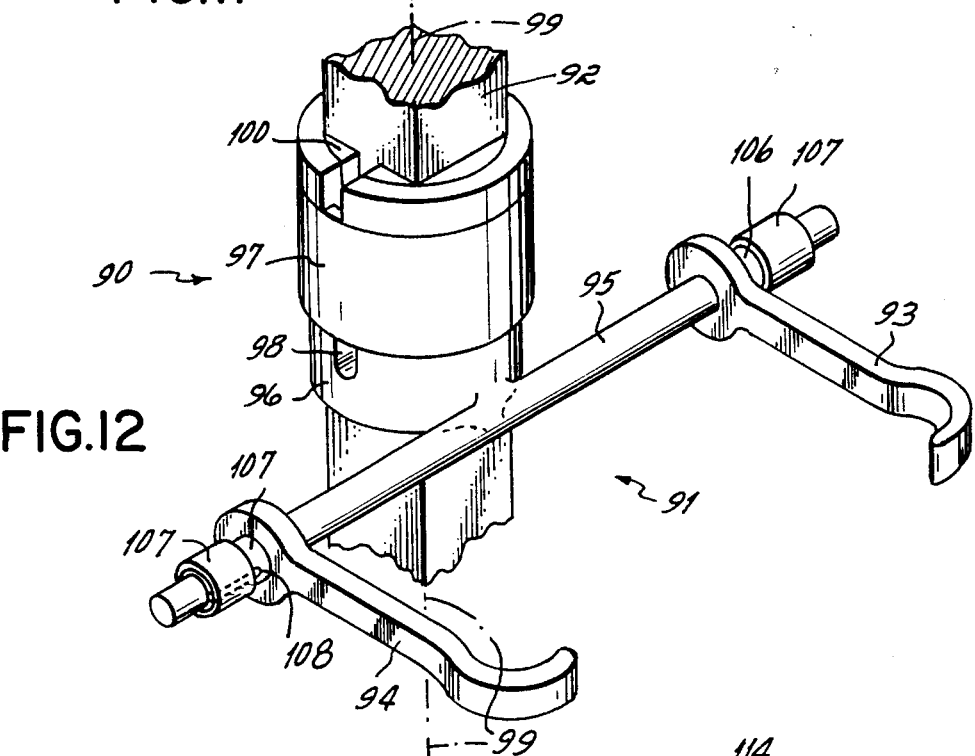
FIG. 12 is a perspective view of a scoliosis correction system according to the present invention.
Figure 13:
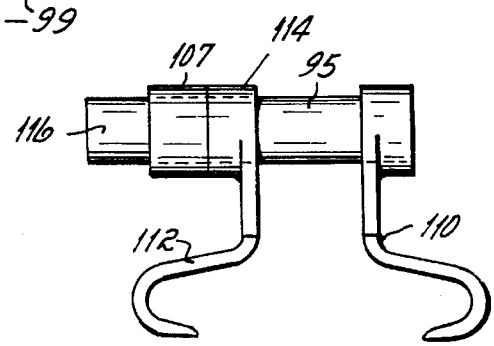
FIG. 13 is an elevational view of a clamping system according to the present invention.

Referring to FIGS. 12–13, a scoliosis correction device 90 incorporating many of the previously described principles of the present invention includes a stabilization or correction rod 92 which is secured along a patient's spine (not shown) with a plurality of clamps 91, each clamp having dual spinal hooks 93 and 94 or so-called interlaminar or pedical hooks. Typically, each set of hooks 93, 94 engage different parts of a single vertebra. The hooks 93, 94 in each clamp 91 are mounted in a spaced apart manner along a pin 95. Each pin 95 is fixed to a tubular section 96 disposed around the correction rod 92. A shape memory ring or sleeve 97, like previous sleeves according to the present invention, is likewise disposed around the outside of tubular section 96. As in the previous embodiments, the tubular section 96 may include one and preferably two longitudinal slots or apertures 98 formed through its walls, for the same reasons as previously described. To help control relative rotation between the tubular section 96 and the rod 92 about a common axis 99, structure similar to that shown in FIGS. 9 and 9A could be used. Alternatively, the rod 92 could be made with a square or otherwise non-circular cross section and disposed inside of a separate tubular sleeve 100 which has a similar non-circular receiving bore. Sleeve 100 is disposed concentrically inside of section 96. Memory ring 97 may be trained so that at temperatures below the TTR, sleeve 100 if free to rotate inside section 96 around axis 99. With sleeve 100 free to rotate in this manner and clamps 91 connected to the patient's spine, a torque could be applied to the rod 92, such as with a wrench, and thereby to the patient's spine. Warming ring 97 to above the TTR would then lock the rod 92, sleeve 100 and section 96 in place, and maintain the torque applied to the patient's spine. With the temperature of ring 97 below the TTR, both sleeve 100 and section 96 are also moveable along the length of rod 92. Likewise, sleeve 100 and section 96 can be fixed at a given point along rod 92 by warming ring 97 above the TTR. Thus, each clamp 91 can be repeatedly adjusted and reliably fixed to any point along the length of rod 92.

Figure 12A:
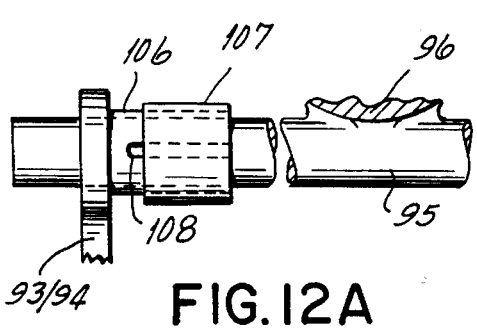
FIG. 12A is an enlarged elevational view of an embodiment according to the present invention for mounting one of the spinal hooks of the system shown in FIG. 12.
Figure 12B:
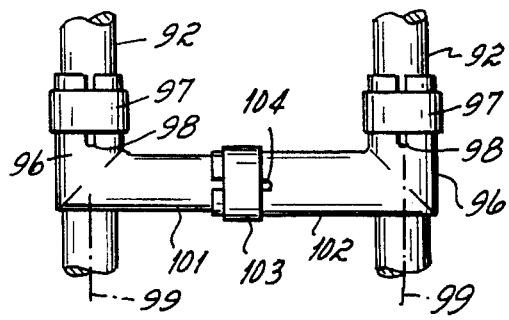
FIG. 12B is a rear view of a Cotrel-Dubousset and Isola system for scoliosis correction according to the present invention.

Referring to FIG. 12B, in a Cotrel-Dubousset and Isola system for scoliosis correction, two rods 92 are mounted on either side of a patient's spine according to the principles of the present invention. The distance between each rod 92 can be made adjustable by using a first element 101 telescopically disposed inside of a second element 102. The depth to which element 101 is disposed inside of element 102, and therefore the distance between rods 92, may be adjusted according to the principles of the present invention. For example, a shape memory ring 103 and a longitudinal slot 104 formed in element 102 may be used in the same manner previously described (see for example FIG. 5c). To adjust the position of each element 101 and 102 on their respective rods 92, each element 101, 102 may include structure like the tubular section 96 and shape memory ring 97 as previously described. Again, it may be desirable to form one or more slots 98 in the wall of tubular sections 96.

Figures 12C, 12D:
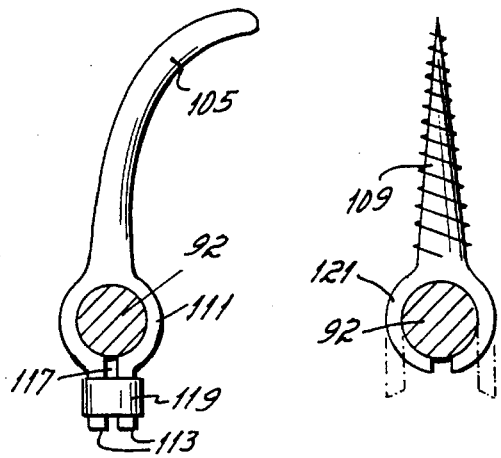
FIG. 12C is a partially sectioned elevational view of a Harrington rod and laminar hook according to the present invention.
FIG. 12D is a partially sectioned elevational view of a Harrington rod and vertebra screw according to an alternative embodiment of the present invention.

Referring to FIGS. 12C and 12D, either rod 92 may be secured along the patient's spine with a plurality of hooks 105 or screws 109, or a combination of both. Each of the hooks 105 or screws 109 may be adjustably secured to the rod 92 utilizing principles of the present invention. For instance, the hook 105 or screw 109 could be mounted to a split ring 111 dimensioned to encircle rod 92. Split ring 111 has two opposing clamping flanges 113 which form a slot 117 therebetween. A shape memory ring 119 is disposed around both clamping flanges 113. Ring 119 may be trained to shrink upon heating above the TTR in order to narrow slot 111 and force split ring 111 to clamp around rod 92. Alternatively, each of the hooks 105 or screws 109 may be mounted to a shape memory split ring 121. Ring 121 may be trained to encircle rod 192 in a gripping manner when at a temperature above the TTR and open up into a U-shape (shown in phantom in FIG. 12D), when at a temperature below the TTR, allowing rod 92 to be easily detached from split ring 121. Thus, the hooks 105 can be positioned against or the screws 109 screwed into the patient's spine and then secured to rod 92 by raising the temperature of the shape memory element to above the TTR.

Hooks 93 and 94 can be similarly adjusted and reliably fixed to points along pin 95 by using similar tubular sections 106, each mounting one hook and disposed concentrically around pin 95, and a shape memory ring or sleeve 107 disposed concentrically around sleeve 106. As in previous embodiments, it may be desirable to form one or more longitudinal slots 108 through the wall of each tubular section 106. Each tubular section 106 and shape memory ring 107 may be attached medially or laterally of its respective hook 93, 94. To reduce space, it may be desirable to position each section 106 and ring 107 along pin 95 medially of its respective hook 93, 94 as shown in FIG. 12A. Adjustment of the distance between hooks 93, 94 during clamping of the correction device 90 to vertebras in a patient's spine can be accomplished using the same techniques incorporating the principles of the present invention previously described.

Figure 13A:
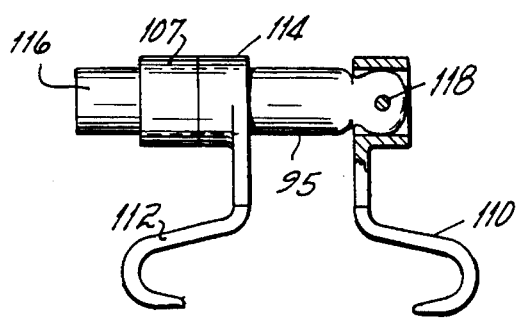
FIG. 13A is a partially sectioned elevational view of an alternative embodiment of the claiming system of FIG. 13 with one hook being pivotal relative to the other hook.
Figure 13B:
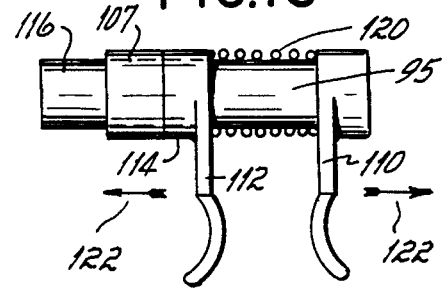
FIG. 13B is a partially sectioned elevational view of an alternative embodiment of the clamping system of FIG. 13 including a biasing spring.

Referring to FIGS. 13, 13A and 13B, it may be desirable to modify the clamps 91 of the correction device 90 by permanently fixing one hook 110 to pin 95 and adjusting the relative distance of another hook 112 in a different manner. In the embodiments shown in these figures, hook 112 is similarly mounted to a tubular section 114 which freely slides along pin 95. Unlike the previous embodiment, however, the shape memory ring 107 is designed to fit only around pin 95. The ring 107 is positioned between the tubular section 114 and a free end 116 of the pin 95. With the ring 107 tightly fixed against pin 95, the hook 112 is only free to move between hook 110 and ring 107. According to the principles of the present invention, as previously described, the relative distance between hooks 110 and 112 can be adjusted by cooling ring 107, moving it to a new position along pin 95 and then heating ring 107 back to ambient or above the TTR, whichever is appropriate.

It may be desirable to make the tubular section 114 out of shape memory material and eliminate the ring 107 entirely. This would enable clamp 91 to be more compact. It may also be desirable to pivotally mount hook 110 to pin 95, such as with a pivot pin 118 (see FIG. 13A). The clamping structure shown in FIG. 13 may also be used in different applications, such as for suture expansion applications. For example, referring to FIG. 13B, a compression coil spring 120 can be disposed concentrically around pin 95 and between hooks 110 and 112. In this way, the spring 120 can provide a force to move the hooks 110, 112 apart (as shown by arrows 122) when ring 107 has been cooled and is movable toward the end 116 of pin 95. Again, it may be desirable for spring 120 to be made of a shape memory material, depending on the application. The clamping structure shown in FIG. 13 and 13A may also be used as an interlaminar clamp. In this application, pin 95 is oriented along the patient's spine and functions as a Harrington rod. Clamps 110 and 112 are then used to secure together two or more laminars in stabilizing a patient's spine.

Figure 14:
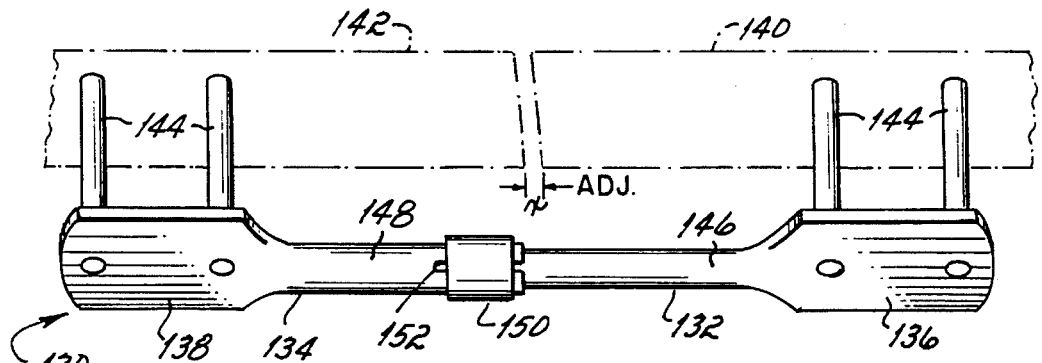
FIG. 14 is a perspective view of a distraction osteogenesis device according to the present invention.
Figure 15:
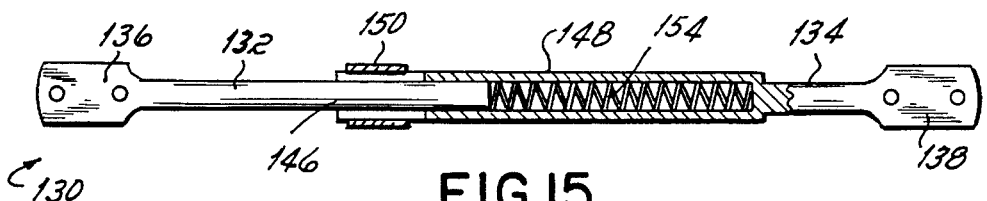
FIG. 15 is a partially sectioned elevational view of an alternative embodiment of the device of FIG. 14 including a biasing spring.

Referring to FIGS. 14 and 15, the principles of the present invention are also applicable to devices like a distraction osteogenesis device 130 having a first element 132 and a second element 134, each of which has a first portion 136 and 138, respectively, such as a mounting plate, for being connected to different respective parts 140 and 142 of a patient's body, such as two parts of the same bone or two different bones (e.g. facial bones). The plates 136, 138 can be mounted to their respective bone parts 140, 142 with any appropriate fastener 144, such as pins, bolts or screws. The first element 132 has a second portion or pin 146 which is telescopically received by a second portion or tubular section 148 of the second element 134 to a variable desired depth. A shape memory ring or sleeve 150, similar to previously described shape memory sleeves, is likewise concentrically positioned around the outside of the tubular section 148 within the region portions 146 and 148 overlap. As with previous embodiments, it may be desirable to form at least one and preferably two longitudinal slots or apertures 152 through the wall of tubular section 148. Sleeve 150 can be treated in the same manner as previous shape memory sleeves in order to repeatedly adjust the depth of pin 146 in tubular section 148 and thereby the separation between body parts 140 and 142.

In some applications, it may be desirable to provide device 130 with a spring 154, such as a coil spring, for applying a force for moving the elements 132 and 134 relative to one another, at least when the temperature of the shape memory ring 150 drops below its transformation temperature range. For the device 130 illustrated in FIG. 15, the coil spring 154 is positioned within the tubular section 148 between the leading end of the pin 146 and the bottom of the tubular section 148. The spring 154 may be a compression spring or a tension spring. If the former, the elements 132 and 134 will be forced apart. If the later, each end of the spring 154 would need to be attached to its respective element 132, 134 in order for the pin 146 to be drawn deeper into the tubular section 148.

The device 130 illustrated in FIGS. 14 and 15 can be easily modified for use in other types of devices having telescoping elements. As an example, for the device 130 of either FIG. 14 or 15 to be particularly useful in a Herbst appliance, the sleeve 150 can be redesigned as a stop (like sleeve 18 in FIG. 3) and repositioned to a desirable location along the pin 146. The spring 154 can be made of any appropriate spring material. Depending on the application, it may be preferable for the spring 154 to be made of a superelastic material, such as a shape memory material, in order to ensure that the spring 154 applies a constant force throughout its through length (i.e., very flat mechanical characteristics). With the spring 154 applying such a constant force, incremental adjustments in the spacing between parts 140 and 142 are possible.

Figure 15A:
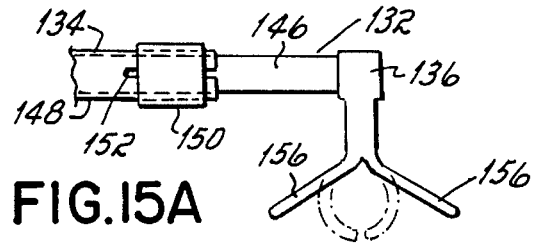
FIG. 15A is a partial elevational view of a telescopic device according to the present invention with two gripping prongs made of a shade memory material mounted thereto.

Referring to FIG. 15A, the first portion 136 of device 130, by way of example, may be made of a shape memory material and have two gripping prongs 156 which are pre-programmed to be in a gripping configuration at ambient temperature.

Figure 16:
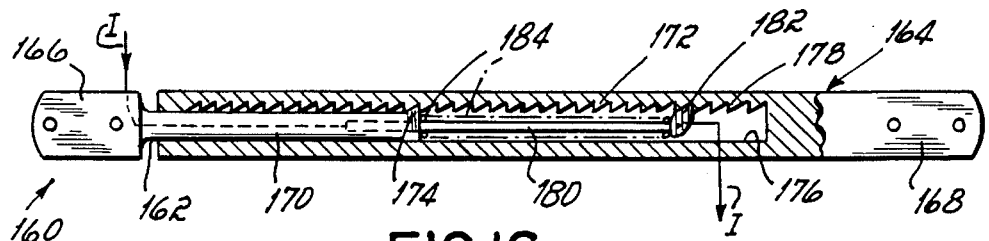
FIG. 16 is a partially sectioned elevational view of an alternative distraction osteogenesis device according to the present invention incorporating a ratcheting system.

Referring to FIG. 16, a ratcheting device 160, for use in applications similar to that of device 130, includes a first element 162 and a second element 164, each having respective first portions 166 and 168 connectable to a body part. The first element 162 has a second portion 170 which is telescopically disposed inside of a second portion 172 of the second element 164 to a variable desired depth. The leading end of the second portion 170 of element 162 mounts a first pawl 174. A second portion 172 of element 164 has an inside surface 176 with a length and a plurality of ratchet teeth 178 formed there along. A third element 180, made of a shape memory material, having a length and opposite ends, is fixed at one end to the leading end of the second portion 170 of element 162. The other end of shape memory element 180 mounts a second pawl 182. A spring 184, such as a coil spring, is disposed around the shape memory element 180, within the inside surface 176 and between the pawls 174 and 182. Both of the pawls 174, 182 are constructed so as to be movable in one direction lengthwise along the inside surface 176 of second portion 172 and lockable against at least one of the ratchet teeth 178 in an opposite direction. One or the other or both of the pawls 174, 182 may need to be pivotally mounted to its respective element in order for there to be such a ratcheting movement of the first and second elements 162, 164 relative to each other in only one direction. In order to have ratcheting movement of portion 170 out of portion 172, the spring 184 can be a compression spring and the third element 180 a shape memory wire that shrinks in length to compress spring 184, when heated above the TTR and is stretchable by spring 180 when cooled to below the TTR.

Therefore, to ratchet portion 170 of element 162 out of portion 172 of element 164, wire 180 is heated until it shrinks in length, pulling the second pawl 182 closer toward the first pawl 174. One way of selectively heating the shape memory element 180 is by passing an electric current, indicated by line I—I, through wire 180. The wire 180 is then allowed to cool down and become elongated by the force exerted by spring 184. Pawl 182 is pivotally mounted to the end of wire 180 in a manner that allows movement of the pawl 182 out of portion 172 but causes the pawl 182 to engage and lock with at least one ratchet tooth 178 when the spring 184 begins to stretch the wire 180. The first pawl 174 is also designed to freely move out of but not deeper into the portion 172 of element 164. Thus, when the shape memory material is cooled to the point that spring 184 is able to stretch wire 180, a positive force is applied to push portion 170 of element 162 out of portion 172 of element 164. As with spring 154 of the modified device 130 (see FIG. 15), spring 184 can be made of any appropriate spring material but for some applications a superelastic material may be preferable.

Referring to FIG. 17 and 17A, a hypodermic needle 185 is connectable to a syringe 186 using the principles of the present invention. The syringe 186 includes a tubular section 187 which telescopically receives the rear end of the needle 185. A shape memory ring 188, like in previous embodiments, is positioned concentrically around the outside of the tubular section 187. As previously described, the shape memory and superelastic characteristics of the ring 188 can be used to allow variable adjustment of the effective length of the needle 185. Again, it may be desirable to form one or more longitudinal slots 189 through tubular section 187. It may also be desirable to make the tubular section 187 or the needle 185, or both, out of shape memory material and eliminate ring 188 using the principles of the present invention described for the structure illustrated in FIG. 11. Thus, the length of needle 185 can be easily adjusted to accommodate a particular medical need rather than having to stock needles 185 of varying lengths.

Referring to FIGS. 18A, B and C, one embodiment of a connecting system 190 incorporating the principles of the present invention includes a mounting bracket or plate 192 having a hole 194 formed therethrough for receiving a portion of a fastener 196, such as a screw. One or the other or both of the fastener and at least a portion 198 (diagrammatically shown in phantom in FIG. 18A) of the plate 192 forming the hole 194 is made of a shape memory material according to the principles of the present invention. It may not be desirable to make the entire plate 192 out of the shape memory material. In that case, portion 198 may be a separate insert fixed to the balance of plate 192 by any suitable method, for example possibly welding. It is desirable for the hole 194 to be formed with at least one and preferably two or more through-notches on its periphery. As shown in FIG. 18A and B, the notches 200 are intended to become narrower and at least attempt to close at least when the portion 198 of plate 192 is heated to the appropriate temperature and to open when it is cooled to the appropriate temperature. Thus, a fastener 196 can be respectively captured or free to move within hole 194. It may also be desirable for the fastener 196 to be more permanently locked in place. In that case, a shape memory material with a wide TTR may be appropriate. While the shape memory properties of the shape memory material can be used to thermally open or close the notches 200, mechanical means, such as spacers inserted into each notch 200, can also be used to keep them open until a fastener 196 is in an acceptable position within hole 194 and, with the shape memory material in its superelastic condition, the spacer removed, the notches 200 allowed to close, and the hole 194 grip the fastener 196.

Referring to FIG. 18C, by using a ball-headed fastener 196 and a hole 194 having a periphery adapted to receive its ball-shaped head 202, the ball-headed fastener 196 can be oriented at a plurality of entry angles to the plate 192. A slot 204 may also be formed in the head 202 for the same reasons previously described for slot 82 shown in FIG. 11.

Referring to FIGS. 19 and 19A, an alternative connecting system 210 includes a bracket or plate 212 having a hole 214 formed therethrough and a face 216. A shape memory sleeve or ring 218 is mounted to the face 216 of plate 212 concentrically with hole 214. The ring 218 has an inside diameter which becomes smaller as the temperature of the shape memory material increases, in accordance with the principles of the present invention. Thus, when a portion 220 of a fastener 222 is inserted through hole 214, ring 218 can be made to repeatedly limit or allow movement of the fastener 222 through hole 214. In an alternative embodiment of system 210, a tubular section 224, with or without longitudinal slots 226, is fixed to the face 216 of plate 212 concentrically with hole 214 and the ring 218 is disposed around the tubular section 224 as taught by the present invention (see FIG. 19B).

Referring to FIG. 20, the principles of the present invention are also applicable to controlling the angular movement between a first and second element 228 and 230 connected at a joint 232 incorporating the principles of the present invention. The joint 232 includes a portion 234 of the first element 228 which is telescopically received by a portion 236 of the second element 230, such as a pin and tubular section, respectively, as taught by the previous embodiments. A shape memory ring or sleeve 238 is disposed around the outside of the tubular section 236, which may include longitudinal slots 240. The sleeve 238 can be used to limit or allow the spatial relationship between elements 228 and 230 to be varied, in the same manner as previously described, including relative rotation of the elements 228 and 230 about a common axis 242 (indicated by angle α). Thus, the principles of the present invention are equally applicable to controlling the angular relationship between two elements connected by a joint.

Referring to FIG. 21, the principles of the present invention are applicable to controlling the spatial relationship between a first element 243 and a second element 244 connected at a lockable ball joint 245 according to the prevent invention. Joint 245 includes a ball section 246 fixed to element 243. Ball 246 is disposed and captured within a ball sleeve 247 fixed to element 244. A slot 248 may be formed through sleeve 247, preferably separating sleeve 247 into two opposing sections. Ball 246 is force fit into sleeve 247. A shape memory ring 249 is disposed around the outside of sleeve 247. Ring 249 is in position to force together the opposing sections of sleeve 247 in a gripping manner against the ball 246, thereby fixing the spatial relationship between the elements 243 and 244. Slot 248 provides additional resiliency to sleeve 247, enabling ball 246 to be more easily locked within sleeve 247 by ring 249.

Referring to FIG. 22, the principles of the present invention are equally applicable to controlling the spatial relationship between two or more articulating members, for example, members 250 and 252. Member 250 has a first element 254 telescopically disposed inside of a tubular end 255 of a second element 256. Adjustment of the depth of element 254 in element 256 is allowed or limited according to the principles of the present invention, such as with a shape memory ring 257 disposed around tubular end 255 and a longitudinal slot 258 formed in tubular end 255. The second member 252 likewise has a first element 260 telescopically disposed inside of a tubular end 262 of a second element 264. Relative movement between elements 260 and 264 may likewise be controlled with a shape memory ring 266 and a longitudinal slot 268. The shank of a ball headed stud 270 is fixed to the first element 254 of member 250. The ball head 271 of stud 270 is disposed in a receiving cavity 272 formed in the second element 264 of member 252, for example in the same manner as the head 202 of screw 196 in hole 194 formed in plate 192, as shown in FIG. 18C. Likewise, the head 271 of stud 270 may also include a slot or aperture (not shown) like slot 204 in head 202. Similarly, one or the other or both of the stud 270 and at least a portion of the second element 264 of member 252 forming the receiving hole 272 for the head 271 of stud 270 may be made of a shape memory material according to the principles of the present invention. Any number of such members may be combined for a given application. For example, a sufficient number of these members can be combined to form a Harrington rod like correction rod 92 shown in FIG. 12, providing addition versatility to the system.

The general principles of the present invention are susceptible to a variety of changes and modifications. For example, referring to FIGS. 23–25, a modified connecting system 280 is shown which may be used in applications similar to that of the connecting system 210 shown in FIGS. 19, 19A and 19B as well as other applications. System 280 includes a first element 282, such as a wire, pin, strip or screw, having a portion 284 disposed inside of a hole 286 adapted to receive the first element 282 and formed through a second element 288, such as a mounting bracket or plate. A recessed area or notch 290 is formed in one surface 293 of the second element 288 and intersects the whole 286 such that the first element 282 passes through the recessed area 290. The notch 290 has a first end 291 and a second end 292. The first element 282 passes through the notch 290 intermediate the ends 291, 292. A third element 294, such as a strip, of shape memory material according to the principles of the present invention is adapted to be disposed within the notch 290. One end 295 of the shape memory element 294 is fixed in place within notch 290 by any suitable mechanical means, such as possibly upsetting portions 296 of the second element 288 along edges of notch 290 adjacent the first end 295 of third element 294. Shape memory element 294 has a free end 297 distal from its fixed end 295.

The shape memory element 294 may be configured and trained in accordance with the principles of the present invention such that at an ambient or working temperature, with the first element 282 removed from the hole 286, its distal end 297 overlaps at least a portion of the opening formed by hole 286 as it enters notch 290. Thus, at least at temperatures below the TTR of the shape memory material of element 294, the first element 282 can be inserted through hole 286 and notch 290 in the direction indicated by arrow 302 a desired amount. Being in a more pliable state at this low temperature, shape memory element 294 may be deflectable at its distal end 297 by the passage of first element 282 through element 288 in direction 302.

The first element 282 can be locked in position within the second element 288 by temperature activating the shape memory element 294 to its preprogrammed or trained shape. The shape memory element 294 forcefully returns, or at least forcefully attempts to return, to its preprogrammed shape at least when its temperature is above the TTR (see FIG. 25). The shape memory element 294 returns with enough force to deform a portion 304 of the first element 282 into that section 306 of notch 290 located between the first element 282 and the end 291 of notch 290. The portion 304 of the first element 282 is sufficiently deformed and thereby locked in place by the shape memory element 294 returning to its preprogrammed shape that movement of the first element 282 in the direction of arrow 308 is prevented, or at least limited to a sufficient degree for the particular application. The first element 282 could also be designed to include a series of openings (not shown) spaced apart along its length, each opening being adapted to receive the distal end 297 of element 294. Thus, instead of deforming the portion 304 of first element 282 in order to lock element 282 in place, the distal end 297 of shape memory element 294 could be inserted into any desired opening along the first element 282, while element 294 is in its pliable state. Shape memory element 294 could then be temperature activated to its trained shape, and with the corresponding increase in strength, the shape memory element 294 would be locked within the chosen opening and first element 282 thereby locked in place.

The first element 282 can be unlocked from the second element 288 and its relative position adjusted by lowering the temperature of the shape memory element 294 enough to allow the distal end 297 of element 294 to be pried out of notch 290 for this purpose. A groove 309 may be formed in the second element 288 contiguous with notch 290. Groove 309 should be dimensioned to enable a hook or other prying element (not shown) to be inserted therein and behind the distal end 297 of the shape memory element 294 a sufficient amount to enable end 297 to be pried out of notch 290, thereby facilitating the passage of the first element 282 out of the second element 288 in the direction 308.

Referring to FIG. 25, the connecting system 280 is useful in a variety of applications, including as part of a Lugue-system 310 for spinal scoliosis correction. In Lugue-system 310, the first element 282 is a wire having one end 312 fixed to the second element 288, which is a bracket. The fixed end 312 of wire 282 is attached to bracket 288 at a point spaced from hole 286 such that wire 282 forms a loop around space 314 when it is inserted through hole 286. Thus, bracket 288 can be attached to the patient's vertebra by encircling wire 282 through and around a lamina and inserting the wire 282 through hole 286. It may be desirable for at least the portion of wire 282 encircling space 314 to be made of a shape memory material which is preprogrammed to curve around and encircle the lamina positioned in space 314. Such a preprogrammed wire 282 would likely make attachment to the lamina easier. The wire 282 is locked within hole 286 as previously described with the lamina (not shown) located in space 314. Bracket 288 may then be interconnected by means not shown with other connecting systems 280 attached to other lamina. Previous Lugue-systems (not shown) utilized a bracket with two spaced apart holes formed therethrough. Each end of a length of wire was inserted through one of the holes to form a loop on one side of the bracket. The two wire ends on the other side of the bracket were twisted together and any excess wire cut off. The twisted wire ends of this previous system have been known to unravel or otherwise fail, and the twisted wire ends irritate surrounding tissue.

Other applications of the connecting system 280 may include locking ligature wires and cerclage wires which have been looped around a body part for attachment thereto (e.g., part of a bone). Connecting system 280 may also be used to lock dental wire in orthodontic brackets. In addition, connecting system 280 may be used as an alternative to the connecting systems shown in FIGS. 18A–1C, 19, 19A and 19B to lock bone screws, anchor pins, bone pins, and the like to the appropriate mounting bracket or plate. In such an application, it may be desirable to make hole 286 oblong (see FIG. 26) so that the first element 282 can be locked in place at any point along the length of oblong hole 286. For some applications, especially when inside the patient's body, it may be desirable for element 294 to be made of a wide hysteresis shape memory material, as previously described. In addition, it may also be desirable for one or the other or both of the first and second elements 282 and 288 to be made of a shape memory material.

Referring to FIG. 26, movement of wire 282 in the direction indicated by arrow 308 may alternatively be prevented, or at least limited, by eliminating notch 290 and element 294, and instead using locking clip 320. Locking clip 320 is generally U-shaped, with two legs 322, 324 spaced apart to form slot 326 therebetween and has a front and back surface 321, 323. A shape memory element 328, such as a strip, has one longitudinal edge 330 fixed by any satisfactory means along leg 322 and a free longitudinal edge 332 distal from edge 330. It may be desirable to recess element 328 into a notch 334 formed in the front surface of leg 322. Shape memory element 328 is trained in a similar manner as shape memory element 294 such that edge 332 extends out beyond leg 322 and into slot 326 at an ambient or working temperature. Thus, with notch 290 and element 294 removed and hole 286 formed completely through the second element 288, the elements 282 and 288 can be connected together by inserting the first element 282 through hole 286 until it extends out beyond surface 293 of element 288. Clip 320 is then positioned around that portion of element 282 extending out of element 288. That is, with the shape memory element 328 cooled below the working temperature to be sufficiently pliable, the first element 282 is disposed within slot 326 and the back surface 323 of clip 320 is in contact with the surface 293 of the second element 288. Because slot 326 is oblong, the first element 282, such as a wire, can be locked in place at any point along the length of slot 326. The oblong shape of slot 326 also enables clip 320 to be used with first elements 282 which are wider than they are thick (e.g. flat strips). The shape memory element 328 is then temperature activated to forcefully return to its preprogrammed shape, thereby deforming, for example by bending or cutting into, first element 282 such that movement by the first element 282 in direction 308 is prevented or at least limited.

From the above disclosures of the general principles and detailed description of exemplary embodiments incorporating principles of the present invention, those skilled in the art will readily appreciate the various changes and modifications to which the present invention is susceptible. Therefore, the scope of the present invention should be limited only by the following claims and equivalents thereof.

What is claimed is:

1. A medical/dental apparatus, comprising:

a first element having a first portion and a second portion spaced therefrom, the first portion of said first element adapted for being connected to a first body part;

a second element having a first portion and a second portion spaced therefrom, the first portion of said second element adapted for being connected to a second body part spaced from said first body part, the second portions of said first and second elements being proximately disposed and overlapping in a first variable spatial relationship;

first variable locking means made of a first shape memory material having a first transformation temperature range for limiting changes of said first spatial relationship at a first working temperature and for allowing changes of said first spatial relationship by one or the other of increasing and decreasing the temperature of said first shape memory material relative to said first working temperature.

2. The apparatus of claim 1, the second portion of said first element being telescopically disposed inside of the second portion of said second element to a variable desired depth, thereby forming an overlapping region of said second portions, and said first variable locking means being a ring positionable around the outside of at least said first element.

3. The apparatus of claim 2 including a biasing sleeve positionable between said ring and said first element, said biasing sleeve being able to bias said ring away from said first element at least when the temperature of said first shape memory material is below said first transformation temperature range.

4. The apparatus of claim 2 including a biasing sleeve positionable around said ring and said ring being positionable around the outside of said first element, said ring providing a gripping force and said biasing sleeve providing additional gripping force at least when the temperature of said first shape memory material is below said first transformation temperature range, said ring being able to overcome said biasing sleeve and expand away from said first element at least when the temperature of said first shape memory material is above said first transformation temperature range.

5. The apparatus of claim 2, said ring being positionable only around the outside of said first element outside of said overlapping region.

6. The apparatus of claim 2, the second portion of said second element being a tubular section, and said ring being positionable around the outside of said tubular section and at least part of said overlapping region.

7. The apparatus of claim 6, said tubular section having a wall and at least one longitudinal slot formed through said wall with said ring and the second portion of said first element overlapping at least a portion of said at least one longitudinal slot.

8. The apparatus of claim 2 wherein said locking ring is positioned around the outside of said second portion of said first element adjacent said second portion of said second element to thereby limit relative telescoping motion between said overlapping second portions.

9. The apparatus of claim 8 further comprising a second locking ring positioned around the outside of said portion of said first element adjacent said first portion of said first element to thereby limit relative telescoping motion between said overlapping second portions.

10. The apparatus of claim 1, at least one of the first portions of said first and second elements including connecting means at least partially made of a second shape memory material having a second transformation temperature range for enabling said at least one of the first portions to be connected to the respective body part at a second working temperature and disconnected therefrom by one or the other of increasing and decreasing the temperature of said second shape memory material relative to said second working temperature.

11. The apparatus of claim 10 said connecting means including two gripping prongs made of said second shape memory material, said prongs being in a gripping configuration at least when the temperature of said prongs is at said second working temperature.

12. The apparatus of claim 10, said first and second elements being parts of a scoliosis correction device, said first element being a correction rod and the first portion of said second element including a clamp securable to a patient's spine by said connecting means.

13. The apparatus of claim 12, said clamp including at least one hook.

14. The apparatus of claim 1, the first portion of each of said first and second element including a fastener.

15. The apparatus of claim 14 including means for pivoting the fastener on one of said first and second elements relative to the other.

16. The apparatus of claim 1, the second portion of said second element being a tubular section, the second portion of said first element being a pin having a free end disposed through said tubular section, said pin mounting a first hook, said tubular section mounting a second hook, and said first shape memory element being a ring positionable around a portion of said pin and being positioned between said tubular section and the free end of said pin.

17. The apparatus of claim 16 including a coil spring disposed around said pin and between said tubular section and said first hook.

18. The apparatus of claim 17 said coil spring being a compression spring for providing a force for separating said hooks.

19. The apparatus of claim 1 including a third element proximately disposed and overlapping at least one of said first portions in a second variable spatial relationship and respectively connectable to one or the other of said body parts, and a second variable locking means made of a second shape memory material having a second transformation temperature range for limiting changes of said second spatial relationship at a second working temperature and for allowing changes to said second spatial relationship by one or the other of increasing and decreasing the temperature of said second shape memory material relative to said second working temperature.

20. The apparatus of claim 19 said third element including a fastener directly connectable to one or the other of said body parts.

21. The apparatus of claim 20 at least one of said first portions including a mounting bracket with a hole formed therethrough for receiving at least a portion of said fastener therein, said second variable locking means including one or the other or both of at least a portion of said mounting brackets surrounding said hole and said at least a portion of said fastener disposed in said hole.

22. The apparatus of claim 20 said second variable locking means being connected to said fastener and adapted for gripping at least one of said first portions at said second working temperature.

23. The apparatus of claim 1 including rotational limiting means, independent of from said first variable locking means, for limiting the rotation of the second portions of said first and second elements relative to one another about a common axis.

24. The apparatus of claim 23, the second portion of said first element being telescopically disposed inside of a hole formed in the second portion of said second element, thereby forming an overlapping region of said second portions, said hole having a cross section perpendicular to said common axis and a depth, the second portion of said first element disposed inside of said hole having a cross section perpendicular to said common axis, and said rotational limiting means including the cross section along at least part of the depth of said hole in said overlapping region being non-circular and the cross section of the second portion of said first element that overlaps the non-circular part of said hole being non-circular, said non-circular portion and non-circular part being non-rotatable one inside the other around said common axis.

25. The apparatus of claims 1 or 23 wherein the second portion of said first element is telescopically disposed inside of the second portion of said second element to a variable desired depth.

26. The apparatus of claim 25 wherein said first variable locking means is a collar positionable around the outside of said first element.

27. The apparatus of claim 26 wherein said locking collar is positioned around the outside of said second portion of said first element adjacent said second portion of said second element to thereby limit relative telescoping motion between said first and second elements.

28. The apparatus of claim 27 further comprising a second locking collar positioned around the outside of said second portion of said first element adjacent said first portion of said first element to thereby limit relative telescoping motion between said first and second elements.

29. The apparatus of claim 23, the second portion of said first element being telescopically disposed inside of a receiving bore of a separate tubular sleeve, said sleeve being disposed inside of a circular hole formed in the second portion of said second element, thereby forming an overlapping region of said second portions and said sleeve, the receiving bore of said sleeve having a depth and a cross-section perpendicular to said common axis, the second portion of said first element disposed inside of said receiving bore having a cross-section perpendicular to said common axis, and said rotational limiting means including the cross-section along at least part of the depth of said receiving bore in said overlapping region being non-circular and the cross-section of the second portion of said first element that overlaps the non-circular part of said receiving bore being non-circular, said non-circular portion and non-circular part being non-rotatable one inside the other around said common axis at least when the temperature of said first shape memory material is above said first transformation temperature range.

30. The apparatus of claim 1 including spring biasing means for moving said first element and said second element relative to one another at least when said first shape memory material is at a temperature which allows changes in said first spatial relationship.

31. The apparatus of claim 30, the second portion of said first element being a pin and the second portion of said second element being a tubular section having a bottom surface therewithin, said pin being telescopically disposed inside of said tubular section to a variable desired depth, and said spring biasing means being a coil spring disposed inside of said tubular section and between said pin and the bottom surface of said tubular section.

32. The apparatus of claim 30, the second portion of said first element being a pin having a free end and stop means connected to said free end, and the second portion of said second element being a tubular section having an opening at one end with second stopping means, said pin being telescopically disposed inside of said tubular section through said opening to a variable desired depth, with said free end being inside said tubular section, and said spring biasing means being a coil spring disposed inside of said tubular section, around said pin and between said first and second stop means, each of said stop means preventing the passage of said coil spring thereby.

33. The apparatus of claim 30, said first element having a first end telescopically disposed through the second portion of said second element, stop means for preventing the passage of said free end back through the second portion of said second element, said first variable locking means being positioned on said first element spaced from said stop means with the second portion of said second element therebetween, said spring biasing means being a coil spring disposed between said first variable locking means and the second portion of said second element and around said first element.

34. The apparatus of claim 1, the second portion of said first element and the second portion of said second element being telescopically disposed relative to one another, said first variable locking means being one or the other or both of at least some of the second portion of said first element and said second element.

35. The apparatus of claim 34, said first variable locking means being at least some of the second portion of said first element telescopically disposed inside of the second portion of said second element and having an aperture formed therethrough, said aperture having a shape which limits changes of said first spatial relationship at least when the temperature of said first shape memory material is at said first working temperature.

36. The apparatus of claim 34, the second portion of said first element being a pin, the second portion of said second element being a tubular section disposed around said pin and said first variable locking means being said tubular section.

37. The apparatus of claim 1, the second portion of said first element mounting a first pawl, said first pawl and the second portion of said first element being telescopically disposed inside of the second portion of said second element to a variable desired depth, the second portion of said second element having an inside surface with a length and a plurality of ratchet teeth formed along said length, said first variable locking means having a length and opposite ends and being disposed inside of the second portion of said second element, one end of said first variable locking means being fixed to the second portion of said first element and the other end of said first variable locking means mounting a second pawl, said first pawl and second pawl each being movable in one direction lengthwise along said inside surface and lockable against at least one of said plurality of ratchet teeth in a direction opposite to said one direction, one or the other or both of said pawls being pivotally mounted to its respective element, said apparatus including spring biasing means mounted between said first and second pawls for forcing the movement of said pawls relative to one another when said shape memory material is at a temperature which allows changes in said first spatial relationship.

38. The apparatus of claim 37, including means for changing the temperature of said first shape memory material to a temperature which allows changes in said first spatial relationship.

39. The apparatus of claim 38, said means for changing the temperature of said first shape memory material being means for passing an electric current through said first shape memory material to induce heat therein.

40. The apparatus of claim 37, said first variable locking means being a wire that shrinks in length when heated above said first transformation temperature range, said second pawl being pivotally mounted to the other end of said wire, and said spring biasing means being a compression coil spring disposed around said wire, within the second portion of said second element and between said pawls.

41. The apparatus of claim 37, said first and second elements being part of a distraction osteogenesis device.

42. The apparatus of claim 1, the second portion of said second element being a plate having a hole formed therethrough, said first element being a fastener, the second portion of said first element being disposed inside of said hole, and said first variable locking means being one or the other or both of the second portion of said first element and at least the portion of said plate forming said hole.

43. The apparatus of claim 42, said first variable locking means being said at least the portion of said plate forming said hole, said hole having at least one through-notch on the periphery thereof, said at least one notch becoming narrower when the temperature of said shape memory material is changed from a temperature which allows changes in said first spatial relationship to said first working temperature.

44. The apparatus of claim 42, the second portion of said first element being a ball-head, said hole having a peripheral surface adapted to receive said ball-head such that said fastener can be pivoted to a plurality of angles relative to said plate when the temperature of said shape memory material is a temperature which allows changes in said first spatial relationship.

45. The apparatus of claim 1, the second portion of said second element including a surface and a hole formed therethrough, said first variable locking means being a ring mounted to said surface concentrically with said hole, said ring having an inside diameter which becomes smaller when the temperature of said shape memory material is changed from a temperature which allows changes in said first spatial relationship to said first working temperature, the second portion of said first element being disposed through said ring and said hole.

46. The apparatus of claim 45, the second portion of said second element including a tubular section fixed to said surface concentrically with said hole, said ring being disposed around said tubular section.

47. The apparatus of claim 1, the second portions of said first and second elements being proximately disposed alongside each other, said shape memory element being a ring disposed around both of said second portions.

48. The apparatus of claim 47, said first and second elements being respectively the inner and outer bow of a face bow.

49. The apparatus of claim 1, the second portions of said first and second elements being mating portions of a joint formed thereby.

50. The apparatus of claim 49, said joint being a ball joint with the second portion of said second element being a ball sleeve and the second portion of said first element being a ball section disposed within said ball sleeve thereby forming an overlapping region.

51. The apparatus of claim 50, said first variable locking means being a ring disposed around the outside of said ball sleeve within said overlapping region.

52. The apparatus of claim 1 comprising a plurality of element sets, each said set of elements including one first element, second element and first variable locking means, and means for interconnecting said plurality of element sets.

53. The apparatus of claim 52, the first element of two of said plurality of element sets each being a rod in a scoliosis correction system, with the second element of each of said two element sets being a tubular section telescopically receiving one of said rods, said tubular sections being connected together by a third element set.

54. The apparatus of claim 1, said second element having a hole formed therethrough with an entrance opening and an exit opening, said first variable locking means having a length, a first end fixed to said second element and a second end distal from said first end, said second end overlapping at least a portion of said exit opening when said first shape memory material is at said first working temperature, said first element being positionable through said hole and past the second end of said first variable locking means at least when said first shape memory material is at a temperature below said first transformation temperature range, and once positioned past said first variable locking means, said first element being lockable in place when said first shape memory material is at said first working temperature.

55. The apparatus of claim 54, said first element having a length and two ends, one end of said first element being fixed to said second element at a point spaced from said hole, the other end of said first element being positionable through said hole.

56. The apparatus of claim 1 including a clip having an opening, said first variable locking means having distal edges, one edge of said first variable locking means being fixed to said clip and the other edge overlapping at least a portion of said opening when said first shape memory material is at said first working temperature, said first element being positionable through a hole formed through said second element past the other edge of said first variable locking means and through the opening of said clip at least when said first shape memory material is at a temperature below said first transformation temperature range, and once positioned past said first variable locking means, said first element being lockable in place when said first shape memory material is at said first working temperature.

57. The apparatus of claim 1, said first and second elements being parts of a face bow, the second portion of said first element being telescopically disposed inside of the second portion of said second element to a variable desired depth, said first variable locking means being positionable around the outside of at least said first element, said first variable locking means returning forcefully to a preprogrammed shape when heated to above said first transformation temperature range, thereby achieving a stable axial connection between said telescoping second portions, and the cooling down of the first shape memory material of said first variable locking means to below said first transformation temperature range changes the characteristics of said first shape memory material such that said second portions can be moved axially with respect to one another.

58. The apparatus of claim 57, one of said second portions being a cylindrical portion having an outside diameter and a length, and said first variable locking means being a ring having an inside diameter, said ring being freely movable over the length of said cylindrical portion at temperatures below said first transformation temperature range, and the inside diameter of said ring becoming smaller than the outside diameter of said cylindrical portion at temperatures above said first transformation temperature range.

59. The apparatus of claim 58 including a biasing sleeve positionable between said ring and said cylindrical portion, said biasing sleeve biasing said ring away from said cylindrical portion by stretching said ring when the temperature of said first shape memory material is below said first transformation temperature range, and said ring overcoming the bias of said biasing sleeve and compressing said biasing sleeve around said cylindrical portion when the temperature of said first shape memory material is above said first transformation temperature range.

60. The apparatus of claim 58, the second portion of said second element being a tubular section, said tubular section having a wall with at least one longitudinal slot formed through said wall, and said ring being positionable around the outside of said tubular section with said ring and the second portion of said first element overlapping at least a portion of said at least one longitudinal slot.

61. The apparatus of claim 57 including rotational limiting means, independent of said first variable locking means, for limiting the rotation of the second portions of said first and second elements relative to one another about a common axis.

62. The apparatus of claim 57 including spring biasing means for moving said first element and said second element relative to one another at least when said first shape memory material is at a temperature which allows changes in said first spacial relationship.

63. The apparatus of claim 1, said first and second elements being parts of a lip bumper, the second portion of said first element being telescopically disposed inside of the second portion of said second element to a variable desired depth, said first variable locking means being positionable around the outside of at least said first element, said first variable locking means returning forcefully to a preprogrammed shape when heated to above said first transformation temperature range, thereby achieving a stable axial connection between said telescoping second portions, and the cooling down of the first shape memory material of said first variable locking means to below said first transformation temperature range changes the characteristics of said first shape memory material such that said second portions can be moved axially with respect to one another.

64. The apparatus of claim 1, said first and second elements being part of a distraction osteogenesis device, the second portion of said first element being telescopically disposed inside the second portion of said second element to a variable desired depth, and said first variable locking means being positionable around the outside of at least said first element, said first and second body parts being separated pieces of bone.

* * * * *